(12) United States Patent
Gollwitzer et al.

(10) Patent No.: US 11,484,277 B2
(45) Date of Patent: Nov. 1, 2022

(54) METHOD FOR COMPRESSION OF BREAST TISSUE

(71) Applicant: Siemens Healthcare GmbH, Erlangen (DE)

(72) Inventors: Helmut Gollwitzer, Erbendorf (DE); Andreas Limmer, Fuerth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 79 days.

(21) Appl. No.: 17/172,437

(22) Filed: Feb. 10, 2021

(65) Prior Publication Data

US 2021/0259647 A1    Aug. 26, 2021

(30) Foreign Application Priority Data

Feb. 20, 2020  (DE) .................. 10 2020 202 205.4

(51) Int. Cl.
*A61B 6/04*    (2006.01)
*A61B 6/00*    (2006.01)

(52) U.S. Cl.
CPC ............ *A61B 6/0414* (2013.01); *A61B 6/502* (2013.01)

(58) Field of Classification Search
CPC ....... A61B 6/502; A61B 6/041; A61B 8/0825; A61B 5/708; A61B 8/4218; A61B 10/0041; A61B 2090/036; A61B 8/403; A61B 90/17; A61B 5/0091; A61B 6/04; A61B 6/40; A61B 8/4209
See application file for complete search history.

(56) References Cited

U.S. PATENT DOCUMENTS

| 2008/0043904 A1 | 2/2008 | Hoernig |
| 2015/0297150 A1 | 10/2015 | Grimbergen et al. |
| 2016/0166217 A1 | 6/2016 | Davis et al. |

FOREIGN PATENT DOCUMENTS

| DE | 102006038163 A1 | 2/2008 | |
| EP | 3613348 A1 * | 2/2020 | ........... A61B 5/0091 |

OTHER PUBLICATIONS

German Office Action dated Oct. 16, 2020.

* cited by examiner

*Primary Examiner* — Don K Wong
(74) *Attorney, Agent, or Firm* — Harness, Dickey & Pierce, P.L.C.

(57) ABSTRACT

A method is for compression of breast tissue arranged between a paddle and a stage of a compression system for a mammography examination. The method includes generating a first compression of the breast tissue by building up a reference compression force by adjusting the paddle relative to the stage; comparing the first compression with a target compression; and adjusting the first compression to the target compression, the adjusting including exertion of a manual force on the paddle.

25 Claims, 7 Drawing Sheets

METHOD FOR COMPRESSION OF BREAST TISSUE

PRIORITY STATEMENT

The present application hereby claims priority under 35 U.S.C. § 119 to German patent application number DE 102020202205.4 filed Feb. 20, 2020, the entire contents of which are hereby incorporated herein by reference.

FIELD

Example embodiments of the application generally relate to a method for compression of breast tissue, in particular for a mammography examination, to a compression system and to a mammography system.

BACKGROUND

Mammography examinations are standard procedures in medical imaging. X-ray images of a breast or breast tissue of a patient are created in the process. For this, the breast tissue of the patient is compressed via a compression system. In particular, the breast tissue is compressed between a stage and a paddle. In particular, the breast tissue is compressed on the stage with the paddle. The stage is typically arranged on a surface or side of an X-ray detector or radiation detector facing the rays. Alternatively, the surface of the X-ray detector is designed as a stage. The side of the X-ray detector facing the rays is the side of the X-ray detector, which faces an X-ray source or radiation source or X-ray tube. The X-ray source typically emits X-ray radiation or radiation, which penetrates the compressed breast tissue and is attenuated in the process. The X-ray radiation attenuated by the breast tissue is typically registered or detected or measured with the X-ray detector.

The paddle can typically be adjusted relative to the stage. In particular, the distance between stage and paddle can be adjusted. A compression of the breast tissue can be varied by adjusting this distance. Typically, the breast tissue is firstly compressed between the paddle and the stage with a pre-set parameter. The pre-set parameter can be, for example, a compression force, which the paddle exerts on the breast tissue. Exerting the compression force causes a compression of the breast tissue. The distance between the paddle and the stage is specified by the compression force and the breast tissue. The compression of the breast tissue by way of the pre-set parameter is typically corrected or adjusted by an operator, for example by an MTRA (medical-technical radiology assistant) or a doctor. A correction or adjustment of the compression typically takes place according to visual, haptic and/or sensitivity criteria.

For correction or adjustment of the compression the operator can typically operate a foot switch and thus adjust the distance between the paddle and the stage. In particular, the compression force is thus adjusted for compression of the breast tissue. Alternatively, a handwheel is typically operated to adjust the distance. Typically, a handwheel of this kind is either coupled directly mechanically to the paddle or electronically to a compression drive. The compression drive adjusts the paddle electronically relative to the stage.

A foot switch of this kind or a handwheel of this kind brings about additional costs in the production of the compression system. In addition, setting the compression of the breast tissue via the foot switch or the handwheel is ergonomic and intuitive to only a limited extent since the operator does not have a direct feeling for the compression force acting on the breast tissue.

SUMMARY

Embodiments of the invention provide a method and a system, therefore, which can inexpensively enable intuitive, ergonomic and manual adjusting of the compression of the breast tissue.

At least one embodiment is directed to a method for compression of breast tissue. At least one embodiment is directed to a compression system for carrying out the method and a mammography system, which comprises the compression system. Preferred and/or alternative, advantageous variants are the subject-matter of the claims.

Below, inventive solutions will be described in relation to both the devices or systems and also in relation to the method. Features, advantages or alternative embodiments mentioned here should likewise also be transferred to the other subject matters and vice versa. In other words, the concrete claims (which are directed, for example, toward a device) can also be developed with the features, which are described or claimed in connection with a method. The corresponding functional features of the method are designed by corresponding concrete modules.

At least one embodiment of the invention relates to a method for compression of breast tissue. The breast tissue is arranged between a paddle and a stage of a compression system for a mammography examination. The method comprises the step of generating a first compression of the breast tissue by building up a reference compression force by way of adjusting the paddle relative to the stage. In a further step, the method comprises comparing the first compression with a predefined target compression. In a further step, the method comprises adjusting the first compression to the target compression, wherein adjusting comprises exerting a manual force on the paddle.

An embodiment of the invention also relates to a compression system for a mammography system, designed to carry out an embodiment of the method and its aspects for compression of breast tissue. The compression system comprises a stage, a paddle, which is designed to compress breast tissue arranged between the paddle and the stage, a first force sensor arranged on the paddle and which is designed to measure a force sum on the paddle, and a control unit, which is designed to generate control signals for generating a first compression and/or a target compression of the breast tissue for a mammography examination.

An embodiment of the invention also relates to a method for compression of breast tissue arranged between a paddle and a stage of a compression system for a mammography examination, comprising:

generating a first compression of the breast tissue by building up a reference compression force by adjusting the paddle relative to the stage;

comparing the first compression with a target compression; and adjusting the first compression to the target compression, the adjusting including exerting a manual force on the paddle.

An embodiment of the invention also relates to a compression system for a mammography system, comprising a stage;

a paddle, designed to compress breast tissue arranged between the paddle and the stage;

a first force sensor arranged on the paddle, designed to measure a force sum on the paddle; and at least one processor, designed to generate control signals for generating at least one of a first compression and a target compression of the breast tissue for a mammography examination, wherein the at least one processor is configured to
    generate the first compression of the breast tissue by building up a reference compression force by adjusting the paddle relative to the stage and compare the first compression with a target compression, subsequent adjusting of the first compression to the target compression including exerting a manual force on the paddle.

An embodiment of the invention also relates to a mammography system comprising an inventive compression system of an embodiment, an X-ray source and an X-ray detector.

BRIEF DESCRIPTION OF THE DRAWINGS

The above-described properties, features and advantages of this invention will become clearer and more comprehensible in connection with the following figures and their descriptions. The figures and descriptions are not intended to limit the invention and its embodiments in any way. Identical components are provided with corresponding reference numerals in different figures. As a rule, the figures are not to scale.

In the drawings.

DETAILED DESCRIPTION OF THE EXAMPLE EMBODIMENTS

Figure 1:
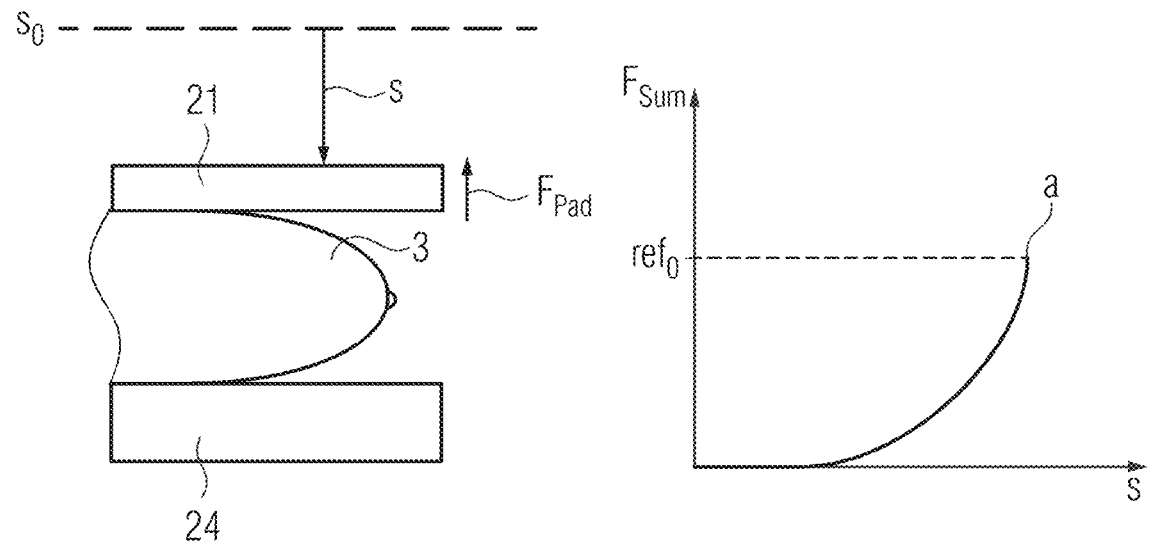
FIG. 1: shows a representation and a graph in one example embodiment of the inventive method for compression of breast tissue, comprising generation of the first compression.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for compression of breast tissue. The breast tissue is arranged between a paddle and a stage of a compression system for a mammography examination. The method comprises the step of generating a first compression of the breast tissue by building up a reference compression force by way of adjusting the paddle relative to the stage. In a further step, the method comprises comparing the first compression with a predefined target compression. In a further step, the method comprises adjusting the first compression to the target compression, wherein adjusting comprises exerting a manual force on the paddle.

In particular, the method for compression of breast tissue is used for a mammography examination. The breast tissue is compressed between the stage and the paddle for this.

The stage can be the surface of an X-ray detector. The surface of the X-ray detector typically comprises an area of approx. 30×24 cm2. Alternatively, the stage can be a plate made from an X-ray permeable material, which is arranged on the side of the X-ray detector facing the rays. X-ray permeable means that the absorption or attenuation of X-ray radiation by the X-ray permeable material is negligible. In this embodiment, the stage typically comprises a rectangular or square surface. For example, the stage can have an area of approx. 35×25 cm2. In particular, the stage is arranged in a geodetically horizontal plane. In particular, the stage is arranged parallel to the surface of the X-ray detector.

The paddle comprises a plate with a rectangular or square surface. In particular, the plate can comprise the same dimensions as the surface of the stage. Advantageously, the plate of the paddle is made from an X-ray permeable material. Advantageously, the material of the plate of the paddle is visually transparent. Visually transparent means that it is possible to see through the material. In particular, the plate of the paddle can be made from an visually transparent plastics material such as PMMA (polymethylmethacrylate). In particular, the paddle also comprises a frame in which the plate of the paddle is arranged. The frame is connected at least to one side of the plate. In particular, the frame can be connected to the plate at three or four sides. In particular, the frame can be detachably or non-detachably connected to the plate. In particular, the frame can be screwed or glued to the plate. Alternatively, the plate can be clamped in the frame.

In particular, the plate of the paddle is arranged parallel to the stage. In particular, the paddle is arranged to be geodetically vertically spaced apart from the stage. In advantageous embodiments, the paddle is arranged above the stage. In alternative embodiments, the paddle is arranged below the stage.

In particular, the breast tissue is arranged between the stage and the paddle.

The distance of the paddle from the stage can be adjusted. In particular, a compression of the breast tissue can be produced by adjusting the distance or by adjusting the paddle relative to the stage. When the distance is reduced, the compression of the breast tissue is increased. When the distance is increased, the compression of the breast tissue is reduced.

The reference compression force can be built up on the breast tissue by adjusting the paddle relative to the stage. The reference compression force is typically pre-set or defined or determined in advance. It can be pre-set manually or (semi-)automatically. In particular, the distance between paddle and stage is adjusted until the paddle presses on the breast tissue with the reference compression force or until the paddle exerts the reference compression force on the breast tissue. The first compression of the breast tissue can be produced by exerting the reference compression force on the breast tissue. In particular, the force produced on the breast tissue by the paddle can be referred to as the paddle compression force. In particular, the breast tissue then also exerts a force with a value of the reference compression force on the paddle. The value of the reference compression force matches the value of reference compression force. In particular, the force on the paddle due to the breast tissue acts in the opposite direction to the reference compression force on the breast tissue due to the paddle.

The first compression is compared in the following step with the target compression. Comparing comprises, in particular, visual and/or haptic criteria. In cooperation with the patient the operator checks whether the first compression of the breast tissue is suitable for carrying out the mammography examination. For example, the operator can check whether the breast tissue is crease-free and/or uniformly compressed or whether the patient is feeling pain. If the first compression is acceptable, the first compression and the target compression match and no further adjustments are necessary. If this is not the case, the first compression has to be adjusted to the target compression.

The step of adjusting the first compression to the target compression comprises exerting the manual force on the paddle.

The manual force is exerted on the paddle by a person in particular. In particular, the manual force is exerted on the paddle by the operator.

In advantageous embodiments, the manual force can comprise pressing on the paddle and/or pulling on the paddle. The pressing or pulling can be performed, in particular, by the operator to adjust the first compression to the target compression. In this case, pressing is exerting the manual force geodetically vertically downwards. Pulling is exerting the manual force geodetically vertically upwards. In other words, pressing comprises a force with at least one vertically downwardly acting force component. The vertically downwardly acting force component then corresponds to the manual force. Analogously, pulling comprises a force with at least one vertically upwardly acting force component. The vertically upwardly acting force component then matches the manual force. In particular, exerting the manual force can cause an adjustment of the paddle relative to the stage, so the first compression is adjusted to the target compression of the breast tissue. In particular, with an arrangement of the paddle above the stage, pressing can cause a stronger compression of the breast tissue. In particular, the distance between the paddle and the stage can be reduced by pressing. Pulling can cause a reduced or lower compression of the breast tissue. In particular, the distance between the paddle and the stage can be increased by pulling. If the paddle is arranged below the stage, pressing and pulling can be in the opposite direction to the above description. In particular, pulling then causes an increase in the first compression and pulling a reduction in the first compression.

In alternative embodiments, the manual force can act on a switch. The switch can be arranged, in particular, on the paddle, in particular on the frame of the paddle. In particular, the switch can be designed as a pressure switch, a toggle switch, a rotary switch, a slide switch, etc. In particular, the switch can be designed as a mechanical switch or an electronic switch. In particular, the switch can be designed as a lever. In particular, the switch can be activated with the manual force. Activating can be carried out by way of pressing, tilting, turning, sliding, etc. Advantageously, two switches are arranged on the paddle. On activation, one of the switches causes the distance of the paddle from the stage to increase. On activation, the other switch causes the distance of the paddle from the stage to reduce. The manual force can be an additional paddle compression force, therefore, which is built up by adjusting the paddle. In particular, the additional paddle compression force can act on the paddle in the same direction as the paddle compression force. Alternatively, the additional paddle compression force can act on the paddle counter to the paddle compression force. The direction of the paddle compression force is dependent on an adjusting direction of the paddle. The adjusting direction indicates whether the distance between paddle and stage is increased or reduced.

The inventors have found that by exerting the manual force on the paddle the first compression can be intuitively adjusted by the operator to the target compression. In particular, when exerting the manual force on the paddle the operator is positioned close to the breast tissue. In particular, the operator can observe the breast tissue during the compression through the advantageously transparent plate of the paddle. The inventors have found, in particular if the manual force comprises pressing or pulling, the operator has an intuitive feeling for a compression force for adjusting the first compression of the breast tissue by the manual force. This increases the patient's comfort since overcontrolling the compression, an excessive compression, in other words, can be avoided thereby. In addition, by positioning the operator close to the patient it is possible to consult the patient directly in order to improve the patient's comfort during the mammography examination.

According to a further embodiment, the method also comprises the step of detecting the force sum acting on the paddle comprising a force with a value of a paddle compression force and the manual force via a first force sensor, which is arranged on the paddle.

In particular, the first force sensor is a sensor, which detects a force, which acts on the first force sensor. In particular, the first force sensor detects the force, which acts vertically on the paddle. In particular, the first force sensor detects the sum of all force components, which act vertically on the paddle. Typically, the first force sensor detects an active force by way of a deformation produced by the active force inside the first force sensor. The first force sensor can be, for example, a spring body force sensor, a capacitive force sensor, a piezo force sensor, an electrodynamic force sensor or a resistive force sensor.

In particular, the paddle compression force is the force, which acts on the breast tissue due to the paddle. In other words, the paddle compression force is the force, which acts on the breast tissue without taking the manual force into account. In particular, the value of the paddle compression force is the amount of the paddle compression force. In particular, the breast tissue then also exerts the force with the value of the paddle compression force on the paddle in order to guarantee a force equilibrium. In other words, the breast tissue presses on the paddle with the same force with which the paddle also presses on the breast tissue in the opposite direction. In particular, the first force sensor detects the forces, which act on the paddle. In particular, the force acts upwardly on the paddle with the value of the paddle compression force due to the breast tissue if the paddle is arranged above the stage. If the paddle is arranged below the stage, the force acts downwardly on the paddle with the value of the paddle compression force due to the breast tissue.

The direction of the respective force is observed in particular when determining the sum of the force with the value of the paddle compression force and the manual force. In particular, the values of the forces are subtracted from one another or added depending on their direction. If the directions of the forces are opposed, their values are subtracted from one another. If their directions are the same, their values are added. The force sum then matches the value of this summation. The value of the manual force matches the amount of the manual force.

In particular, the step of detecting the force sum can be carried out at any desired points in the above-described method. In particular, the step of detecting the force sum can be carried out more than once in the above-described method. In particular, detecting the force sum is carried out at least on generating the first compression and on adjusting the first compression.

On generation of the first compression, the manual force is zero. In other words, there is no manual force acting on the paddle. In particular, the first force sensor then registers only the value of the paddle compression force. In other words, the force sum matches the value of the paddle compression force. For generating the first compression the paddle compression force in particular is equal to the reference compression force. In particular, it is therefore possible to check with the first force sensor at which distance between paddle and stage the paddle compression force is equal to the reference compression force.

On exertion of the manual force on the paddle, the first force sensor measures a change in the force sum on the breast tissue. Before exerting the manual force, the force sum is equal to the value of the reference compression force. During exertion of the manual force, the force sum is greater than or less than before exertion of the manual force depending on the direction of the manual force. In particular, the operator can bring about a change in the force sum in this way by way of the manual force, and this triggers adjusting of the first compression to the target compression. In particular, in this way it is possible to detect, for example, whether the operator wants to increase or reduce the compression of the breast tissue compared to the first compression.

If the paddle is arranged above the stage, pressing on the paddle results in a reduction of the force sum. Pulling on the plate results in a reduction in the force sum.

The first force sensor is typically part of a compression system to enable a first compression with a specified reference compression force of the breast tissue. The inventors have found that via the first force sensor it is possible to detect the change in a compression force due to exertion of the manual force without further elements or components compared to a typical compression system. In particular, the inventors have found that an inexpensive solution to intuitive adjusting of the first compression can be provided, therefore since existing elements such as the first force sensor can be used.

In a further embodiment of the method, the step of adjusting the first compression comprises a first substep, which is carried out during exertion of the manual force on the paddle. The first substep comprises adjusting a paddle position as a function of the force sum detected by the first force sensor, so the force sum again matches the value of the reference compression force.

In particular, the paddle position describes the position of the paddle relative to the stage. In particular, the paddle position characterizes the vertical distance of the paddle from the stage. In particular, the distance of the paddle from the stage and therewith the compression of the breast tissue can be changed by adjusting the paddle position.

In particular, the force sum before exertion of the manual force is equal to the value of the reference compression force. In particular, at this instant the paddle compression force matches the reference compression force. In particular, depending on the direction of the manual force, the force sum is reduced or decreased or increased or enlarged, due to exertion of the manual force, compared to the value of the reference compression force. If the paddle is arranged, for example, above the stage, pressing on the paddle, in other words, exerting the manual force vertically downwards, causes a decrease or reduction in the force sum compared to the value of the reference compression force. In particular, the manual force then acts on the paddle in the opposite direction to the force exerted by the breast tissue with the value of the paddle compression force. Analogously, pulling, in other words a vertical force upwards, causes an increase in the force sum compared to the value of the reference compression force. In particular, the manual force on the paddle and the force exerted by the breast tissue with the value of the paddle compression force then act in the same direction. If the paddle is arranged below the stage, pressing and pulling act in the opposite direction to the effect according to the above description.

In particular, adjusting the paddle position as a function of the force sum means the following:

With a reduction in the force sum compared to the value of the reference compression force due to exertion of the manual force, the distance between paddle and stage is advantageously reduced to increase the force sum on the paddle. The distance is reduced until the force sum is again equal to the value of the reference compression force. A reduction in the distance causes a greater force on the paddle due to the breast tissue. In particular, the paddle compression force is then greater than the reference compression force.

With an increase in the force sum compared to the value of the reference compression force due to exertion of the manual force, the distance between paddle and stage is advantageously increased to reduce the force sum on the paddle. The distance is increased until the force sum is again equal to the value of the reference compression force. An increase in the distance causes a lower force on the paddle due to the breast tissue. In particular, the paddle compression force is then lower than the reference compression force.

In particular, "as a function of the force sum" means, therefore that an adjusting direction of the paddle and/or a stretch by which the paddle is vertically adjusted, depends on the force sum compared to the value of the reference compression force, or is specified/determined by the force sum compared to the value of the reference compression force. The adjusting direction describes whether the distance between paddle and stage is increased or decreased. The stretch describes by how much the distance is increased or decreased.

In particular, the paddle compression force can be increased or reduced in this way by the exertion of the manual force on the paddle. In particular, the paddle compression force can be adjusted by the operator in this way. In particular, the first compression of the target compression can be adjusted in this way.

The inventors have found that intuitive adjusting of the first compression is enabled with the aid of the existing sensor system of the paddle, therefore. The existing sensor system of the paddle comprises the first force sensor. In particular, an inexpensive possibility for intuitive adjusting of the first compression of the breast tissue can be provided, therefore.

In a further embodiment of the method, the step of the adjusting the first compression comprises second and third substeps, which are carried out in order after the first substep. The second substep comprises removing the manual force. The third substep comprises adjusting the value of the reference compression force to the force sum.

In particular, the manual force can be removed after adjusting the paddle position. In particular, the operator advantageously then no longer touches the paddle. In particular, the operator does not then exert a manual force on the paddle. In particular, if the paddle position was previously adjusted by the exertion of the manual force, the paddle compression force no longer matches the reference compression force. In particular, after removing the manual force, the force sum is equal to the value of the paddle compression force.

In the following step, the value of the reference compression force is adjusted to the force sum after removing the manual force. In other words, the value of the reference compression force is replaced by the force sum after removing the manual force. In particular, after adjustment, the paddle compression force then matches the reference compression force again. In particular, after removing the manual force, there is no further adjustment of the paddle position before the value of the reference compression force was replaced by the force sum.

The inventors have found that in this way, the first compression of the breast tissue can be adjusted corresponding to the target compression. In particular, the method enables a re-calibration of the reference compression force according to the specific requirements on compression of the breast tissue of a patient, therefore.

In a further embodiment of the method, the step of adjusting the first compression to the target compression is only carried out if the difference between the value of the reference compression force and the force sum exceeds a predefined threshold value.

In other words, the value of the manual force has to fall below a particular threshold value for the step of adjusting the first compression to be carried out. For example, a threshold value of this kind can be 5N (newtons).

The inventors have found that the threshold value prevents simple touching of the paddle alone resulting in an adjustment of the first compression, in particular resulting in an adjustment of the paddle position. This prevents unnecessary adjustment of the paddle relative to the stage. In particular, this prevents a paddle position which has already been adjusted from being adjusted accidentally. In particular, accidental adjustment of the paddle position can be unpleasant for a patient.

In a further embodiment, the method also comprises the step of detecting whether a manual force is acting on the paddle.

In particular, the step of detecting comprises an assurance that a change in the force sum relative to the value of the reference compression force is generated due to exertion of a manual force by the operator. In particular, it can thus be ensured that, for example, an article which falls onto the paddle does not trigger adjustment of the first compression. In other words, the step of detecting can establish whether a force on the paddle in addition to the paddle compression force is a manual force due to the operator or, for example, a weight of an article.

In particular, the step of detecting can be carried out before the step of adjusting the first compression.

The inventors have found that an assurance of this kind prevents incorrect adjusting of the paddle position. In particular, the inventors have found that, for example, an article which falls onto the paddle can result in an unpleasant or painful adjustment of the first compression of the breast tissue. In particular, the step ensures that a force on the paddle in addition to the paddle compression force is a manual force provided for an adjustment of the first compression intended by the operator.

According to a further embodiment, the step of detecting takes place via a capacitive sensor arranged on the paddle.

In particular, a capacitive sensor is a sensor, which detects a change in the electrical capacitance of at least one capacitor. In particular, the electrical capacitance can be changed by contact of the capacitive sensor with a conductive object or article. In particular, a person touching the capacitive sensor can result in a change in the electrical capacitance. In particular, contact with the capacitive sensor made by dry, non-conductive articles does not result in a change in the electrical capacitance.

In particular, during exertion of the manual force the operator has to touch the capacitive sensor and trigger a change in the capacitance for the first compression to be adjusted according to the above-described method. In particular, it can thus be ensured that a force on the paddle in addition to the paddle compression force is actually a manual force, which is exerted by the operator. In particular, adjusting of the first compression is only carried out when the capacitive sensor detects by way of a touch that a manual force is acting on the paddle. In particular, the capacitive sensor also makes it possible to differentiate between an unintentional force due to touching of the paddle and a manual force for adjusting the first compression. In the case of an unintentional force, a person exerts a force on the paddle unintentionally. However, he/she does not typically touch the capacitive sensor in the process. No adjustment of the first compression is carried out, therefore. In particular, the capacitive sensor makes it possible to differentiate between a manual force and a force, which acts on the paddle due to an article. The article typically does not bring about a change in the electrical capacitance at the sensor. No adjustment of the first compression is carried out, therefore.

The inventors have found that in the case of a force on the paddle in addition to the paddle compression force, it is possible to differentiate between a manual force and a force due to an article or an unintentional force via a capacitive sensor.

According to a further embodiment, the step of detecting takes place via a second force sensor arranged on the paddle.

In particular, the second force sensor can be designed according to one of the embodiments of the first force sensor. In particular, the second force sensor registers or detects only the manual force, which acts on the paddle. In particular, the second force sensor does not register the paddle compression force. In particular, the operator has to touch the paddle at a particular point for the second force sensor to be able to detect the manual force exerted by the operator. In particular, the step of adjusting the first compression is only carried out when the second force sensor detects the manual force. In particular, this can prevent a force acting on the paddle due to an article or an unintentional force from being identified as a manual force if the force of the article or the unintentional force is not acting on the paddle at the corresponding point of the second force sensor.

The inventors have found that it is possible to differentiate a manual force from a force due to an article by way of the second force sensor. In particular, the inventors have found that the size of the manual force can also be detected by a second force sensor. In particular, removal of the manual force can also be detected directly by the second force sensor.

According to a further embodiment, the step of detecting can take place via a switch arranged on the paddle.

In particular, the switch can be designed as a pressure switch, a toggle switch, a rotary switch, a slide switch, etc. sein. In particular, the switch can be designed as a mechanical switch or an electronic switch. In particular, the switch can be designed as a lever.

In particular, the operator has to activate the switch during exertion of the manual force on the paddle for the step of adjusting the first compression to be carried out. Activating can be carried out via pressing, tilting, turning, sliding, etc. In particular, by way of activation of the switch a force, for example due to an article or an unintentional force due to touching of the paddle, can be differentiated from a manual force for adjusting the first compression. In particular, the step of adjustment of the first compression is only carried out when the switch is activated during exertion of the manual force. In particular, the switch is not activated in the case of an unintentional force on the paddle or a force on the paddle due to an article. Only a manual force on the paddle with simultaneous activating of the switch results in adjusting of the first compression, therefore.

The inventors have found that a switch for detecting a manual force provides an inexpensive possibility for identifying whether a manual force is actually acting on the paddle. In particular, the switch provides an inexpensive possibility for preventing unintentional adjustment of the first compression.

According to a further embodiment of the method, the step of adjusting the value of the reference compression force to the force sum is only carried out when the force sum is less than or equal to a predefined maximum compression force value. If the force sum is greater than the value of the predefined maximum compression force, however, the value of the reference compression force is adjusted to the maximum compression force value.

In particular, the predefined maximum compression force value is a standard value. In particular, the maximum compression force value is currently 200N. In particular, according to the standard, a compression of breast tissue via automatic compression may be carried out with a compression force to a maximum of 200N. In particular, the value of the paddle compression force may be, at most, the maximum compression force value, therefore. In particular, the value of the reference compression force may be, at most, the maximum compression force value, therefore. In particular, the maximum compression force value may not be exceeded via a manual compression with the manual force. After removing the manual force the breast tissue may be compressed, at most, with the maximum compression force value.

In particular, this embodiment of the method can prevent the value of the reference compression force being adjusted to the excessive force sum due to exertion of the manual force, as a result of which the force sum becomes greater than the maximum compression force value.

In particular if the force sum during exertion of the manual force is greater than the maximum compression force value, the value of the reference compression force is adjusted to the maximum compression force value in the step of adjusting the value of the reference compression force.

The inventors have found that the embodiment of the method guarantees adherence to the standards. In particular, excessive compressing of the breast tissue can thus be prevented. In particular, the inventors have found that apart from the step of adjusting the value of the reference compression force to the value of the force sum, all other steps of the method can be inventively carried out when the maximum compression force value is exceeded.

According to a further embodiment of the method, the target compression fulfils at least one of the following criteria:

crease-free compression of the breast tissue,
uniform compression of the breast tissue, and/or
pain-free compression of the breast tissue.

In particular, the criteria is evaluated or assessed by the operator or the patient. In particular, the assessment is made visually, haptically or according to the pain perception by the patient.

In particular, the breast tissue should be compressed in a crease-free manner. In particular, compression is suspended again if the breast tissue is not being compressed in a crease-free manner. Advantageously, the operator can smooth the breast tissue during adjustment of the first compression since the adjustment is carried out directly on the paddle. In particular, it is possible to visually assess by way of the advantageously visually transparent plate of the paddle whether the breast is being compressed in a crease-free manner.

In particular, the breast tissue should be uniformly compressed. In particular, the breast tissue should be uniformly compressed at the breast wall side through to the nipple. In particular, for example, a uniform compression can be achieved by increasing the paddle compression force or the reference compression force. In particular, it is possible to evaluate by way of the advantageously visually transparent plate of the paddle whether the breast tissue is uniformly compressed.

In particular, the compression should be painless for the patient. In particular, a direct consultation with the patient is possible for this purpose. In particular, adjusting the first compression on the paddle makes it possible, for example, for the patient herself to reduce the reference compression force until she does not feel any pain.

The inventors have found that all known criteria in respect of the target compression can be fulfilled with the inventive method.

According to a further embodiment, the above-mentioned steps of the method are carried out in a control loop.

In particular, the steps of the method and the steps according to the aspects of the method can be carried out in a control loop. In particular, the control loop comprises at least comparing the first compression with the target compression and adjusting the target compression to the first compression. In particular, the control loop can comprise all further embodiments of the method.

In particular, the control loop can be carried out until the first compression matches the target compression. In particular in this case, the step of comparing the first compression with the target compression results in a match. In particular, the control loop can then be interrupted.

The inventors have found that the execution of the control loop allows the first compression to iteratively approach the target compression.

An embodiment of the invention also relates to a compression system for a mammography system, designed to carry out an embodiment of the above-described method and its aspects for compression of breast tissue. The compression system comprises a stage, a paddle, which is designed to compress breast tissue arranged between the paddle and the stage, a first force sensor arranged on the paddle and which is designed to measure a force sum on the paddle, and a control unit, which is designed to generate control signals for generating a first compression and/or a target compression of the breast tissue for a mammography examination.

In particular, the stage, the paddle and the first force sensor are designed as described above.

In particular, the control unit is designed to control adjusting of the paddle position or adjusting of the paddle relative to the stage. In particular, the control signals from the control unit are used for controlling the paddle position. In particular, control can take place inter alia as a function of parameters such as the value of the force sum, the value of the reference compression force and/or the maximum compression force value. "As a function of" means that the control unit is designed to generate control signals as a function of these values. In this respect the control unit is designed to register or receive above-mentioned parameters via methods and/or interfaces known per se. In particular, control takes place as a function of the force sum measured by the first force sensor. The control signals can be, in particular, electrical, magnetic or mechanical signals.

According to a further embodiment of the invention, the paddle comprises a capacitive sensor, which is designed to recognize a touch.

In particular, the capacitive sensor can be designed as described above. In particular, it is possible to register by way of recognition of the touch whether a force on the paddle is a manual force. In particular, touching the capacitive sensor can trigger a control signal from the control unit, which starts the adjusting of the first compression.

The inventors have found that the capacitive sensor provides an assurance against unintentional adjusting of the first compression. In particular, the inventors have found that information from the capacitive sensor about a touch can be detected, evaluated and processed further by the control unit.

According to a further embodiment of the invention, the paddle comprises a second force sensor, which is designed to detect the manual force on the paddle.

In particular, the second force sensor can be designed as described above. In particular, the second force sensor is designed to detect only the manual force on the paddle. In particular, the manual force on the paddle can be detected if the paddle is touched at the second force sensor. In particular, the second force sensor can detect the size of the manual force. In particular, detecting the manual force on the second force sensor can trigger a control signal from the control unit, which starts the step of adjusting the first compression.

The inventors have found that the second force sensor provides an assurance against unintentional adjusting of the first compression. In particular, the inventors have found that information from the second force sensor about the manual force can be registered, evaluated and processed further by the control unit.

According to a further embodiment of the invention, the paddle comprises a switch, which is designed to register the manual force.

In particular, the switch can be designed as described above. In particular, the switch can be activated during exertion of the manual force. It is possible to identify via the switch whether a force on the paddle is a manual force, therefore. In particular, activating the switch can trigger a control signal from the control unit, which starts the step of adjusting the first compression.

The inventors have found that the switch provides an assurance against unintentional adjusting of the first compression. In particular, the inventors have found that the switch comprises an inexpensive possibility for detecting the manual force.

An embodiment of the invention also is directed to a mammography system comprising an inventive compression system of an embodiment, an X-ray source and an X-ray detector.

In a preferred variant embodiment, the X-ray detector is a flat panel detector or X-ray flat panel detector. This can be a semiconductor detector or a scintillation detector. In a preferred embodiment, the X-ray detector is a digital X-ray detector.

Advantageously, the X-ray source is a rotating anode X-ray tube. Alternatively, the X-ray source can also be a transmission anode X-ray tube. The X-ray source comprises an exit window from which the X-ray radiation advantageously exits as a cone beam.

In particular, the X-ray source and the X-ray detector can be arranged on a stand. In particular, the X-ray source and the X-ray detector are arranged vertically spaced apart. Advantageously, the X-ray source is arranged above the X-ray detector.

In particular, the compression system is arranged between the X-ray detector and the X-ray source. In particular, the compression system is arranged on the stand. In particular, the compression system is arranged in such a way that X-ray radiation emitted by the X-ray source penetrates the compressed breast tissue before it is detected by the X-ray detector.

In particular, the stage of the compression system can be a surface of the X-ray detector or be arranged on the surface of the X-ray detector. The surface of the X-ray detector is the side of the X-ray detector facing the rays. In particular, the surface of the X-ray detectors is the side, which faces the X-ray source. In particular, the vertical distance between paddle and X-ray source is less than between stage and X-ray source.

FIG. 1 shows a representation and a graph in an example embodiment of the inventive method for compression of breast tissue 3, comprising generation of the first compression.

A representation of a breast tissue 3, which is compressed between a paddle 21 and a stage 24, can be seen on the left side of the figure. In particular, the paddle 21 builds up a paddle compression force on the breast tissue 3. In particular, the breast tissue 3 then exerts a force on the paddle with the value of the paddle compression force $F_{Pad}$ in the opposite direction. In other words, the breast tissue 3 presses from below, with a force corresponding to the value of the paddle compression force $F_{Pad}$, against the paddle 21. This force and its direction are represented by the arrow. The force acts, starting from the breast tissue, in the direction of the paddle 21. In particular, the value of the paddle compression force, which the paddle 21 exerts on the breast tissue 3, is exactly as large, therefore as the force with the value of the paddle compression force $F_{Pad}$, which the breast tissue 3 exerts on the paddle 21. In particular, only the directions or signs are reversed. In particular, the value of the paddle compression force $F_{Pad}$ can then be increased by reducing the distance between paddle 21 and stage 24. In particular, the paddle position can be given as a distance s from a zero position $s_0$ of the paddle 21. If the paddle 21 is in its zero position so, then the breast tissue 3 is not compressed. The greater the distance from the zero position so, in other words, the smaller the distance of the paddle 21 from the stage 24 becomes, the more strongly the breast tissue 3 is compressed, or the greater the value of the paddle compression force $F_{Pad}$ is.

FIG. 1 (right) also shows a distance-force graph of step a "generating the first compression". The distance s of the paddle 21 from its zero position $s_0$ is shown on the abscissa. The force sum $F_{Sum}$ is shown on the ordinate. The force sum $F_{Sum}$ is the amount of the sum of the force with the value of the paddle compression force $F_{Pad}$, which is exerted on the paddle 21 by the breast tissue 3, and a manual force $F_m$, which is exerted on the paddle 21 by an operator or the patient. In step a, the breast tissue is compressed until the force sum $F_{Sum}$ matches the value of the reference compression force $ref_0$. Since no manual force $F_m$ acts or is exerted, the value of the paddle compression force $F_{Pad}$ also matches the value of the reference compression force $ref_0$.

Figure 2:
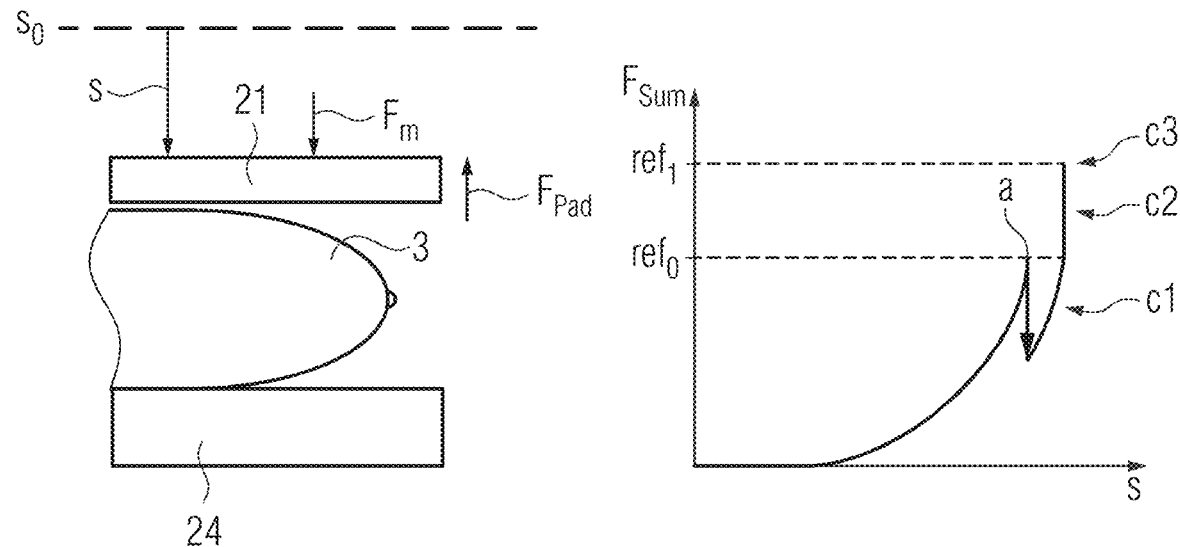
FIG. 2: shows a representation and a graph in one example embodiment of the method according to FIG. 1 comprising an adjustment of the first compression by pressing on a paddle.

FIG. 2 shows a representation and a graph in an example embodiment of the method according to FIG. 1 comprising an adjustment of the first compression by pressing on a paddle 21.

The representation on the left side of the Figure is analogous to the representation on the left side of the FIG. 1. However, after carrying out step a, a manual force $F_m$ is exerted on the paddle 21 here. In particular, the manual force $F_m$ is exerted on the paddle 21 by pressing. In particular, the manual force $F_m$ acts vertically downwards. In particular, the manual force $F_m$ acts counter to the paddle compression force $F_{Pad}$, which acts on the paddle 21 due to the breast tissue 3. The arrow with the marking $F_m$ describes the direction of the manual force $F_m$.

In particular, pressing on the paddle 21 causes a decrease or reduction in the force sum $F_{Sum}$. The decrease is shown on the left of the graph by the arrow beginning at step a. The paddle position is adjusted in substep c1. In particular, the paddle position is adjusted in such a way that the force sum $F_{Sum}$ again matches the value of the reference compression force $ref_0$. In particular, the distance s of the paddle 21 from the zero position $s_0$ is increased for this purpose. The compression of the breast tissue 3 is increased as a result. Substep c3 comprises removing the manual force $F_m$. The force sum $F_{Sum}$ is equal to the value of the paddle compression force $F_{Pad}$ as result. Since the value of the paddle compression force $F_{Pad}$ was increased by adjusting the paddle position in step c1, following removal of manual force $F_m$ the force sum $F_{Sum}$ is greater than the value of the reference compression force $ref_0$.

In substep c3, the value of the reference compression force is adjusted to the force sum $F_{Sum}$. In other words, the value of the reference compression force is set to the new or adjusted value $ref_1$.

The first compression of the breast tissue set in step a can be increased by pressing on the paddle 21, therefore. In other words, the value of the reference compression can be re-adjusted or calibrated by exerting the manual force $F_m$ vertically downwards on the paddle 21.

Figure 3:
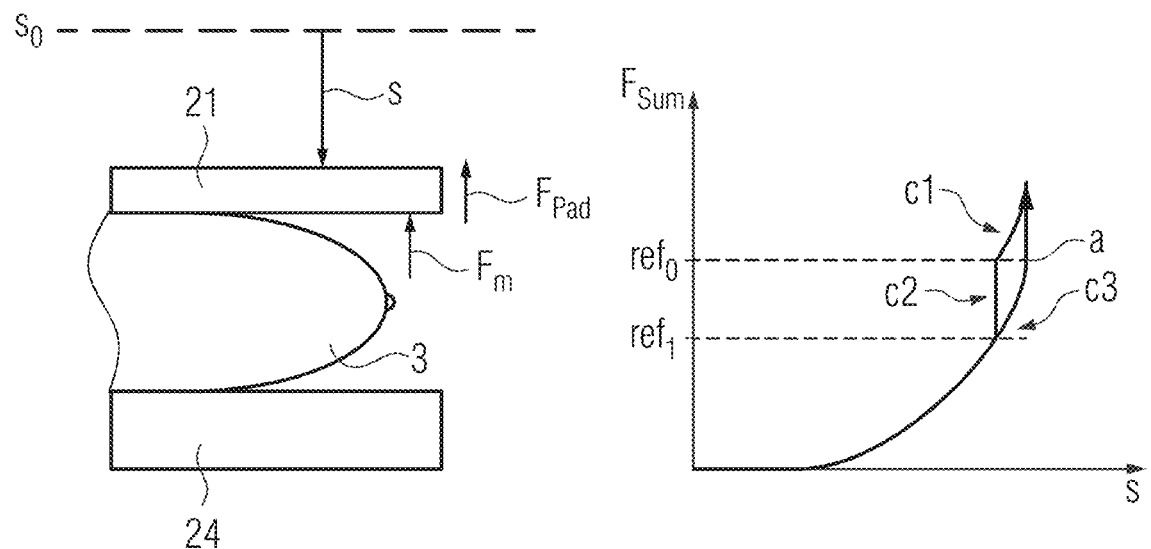
FIG. 3: shows a representation and a graph in one example embodiment of the method according to FIG. 1 comprising an adjustment of the first compression by pulling on the paddle.

FIG. 3 shows a representation and a graph in an example embodiment of the method according to FIG. 1, comprising an adjustment of the first compression by pulling on the paddle 21.

In principle, the method follows the steps as described in FIG. 2. After a first compression of the breast tissue 3 with a reference compression force $ref_0$ has been set in step a, a manual force $F_m$ is exerted on the paddle 21. In this case the manual force $F_m$ is exerted by pulling on the paddle 21. In particular, the manual force $F_m$ acts vertically upwards, therefore. In particular, the manual force $F_m$ and a force with the value of the paddle compression force $F_{Pad}$, which is exerted on the paddle 21 due to the breast tissue 3, act in the same direction. This leads to an increase in a force sum $F_{Sum}$. This increase is shown in the graph on the right side of the Figure by the arrow.

In step c1, the paddle position is adjusted by adjusting the distance s of the paddle 21 from its zero position $s_0$ in such a way that the force sum $F_{Sum}$ matches the value of the reference compression force $ref_0$. The distance s between the zero position $s_0$ and the paddle 21 is reduced for this. The value of the paddle compression force $F_{Pad}$ is reduced as a result.

In substep c2, the manual force $F_m$ is removed. The value of the force sum $F_{Sum}$ becomes smaller than the value of the reference force $ref_0$ as a result.

In substep c3, the value of the reference force is replaced by the force sum $F_{Sum}$ after removing the manual force $F_m$. In particular, the value of the reference force then matches $ref_1$.

The compression of the breast tissue 3 can be reduced by pulling on the paddle 21, therefore.

Figure 4:
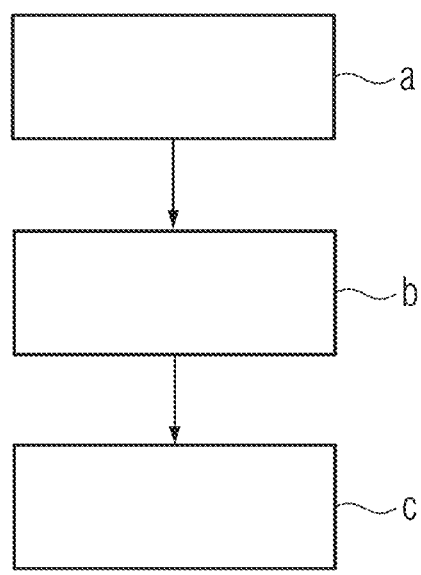
FIG. 4: shows a first flowchart of a further example embodiment of the inventive method for compression of breast tissue.

FIG. 4 shows a first flowchart of a further example embodiment of the inventive method for compression of breast tissue 3.

Step a of the illustrated example embodiment comprises generating a first compression of the breast tissue 3 by building up a reference compression force $ref_0$ by adjusting a paddle 21 relative to a stage 24. In particular, the breast tissue 3 can be compressed by reducing the distance between the paddle 21 and the stage 24. In particular, the distance between the paddle 21 and the stage 24 is adjusted until the value of a paddle compression force $F_{Pad}$ exerted on the breast tissue 3 by the paddle 21 matches the value of a reference compression force $ref_0$.

Step b of the illustrated example embodiment comprises comparing the first compression with a target compression of the breast tissue 3. In particular, the target compression of the breast tissue 3 should fulfil at least one of the following criteria:
crease-free compression of the breast tissue 3,
uniform compression of the breast tissue 3, and/or
pain-free compression of the breast tissue 3.

Fulfilling of the criteria is assessed or evaluated by an operator or the patient. In particular, the evaluation takes place according to visual, haptic and sensitivity criteria. In particular, the compression of the breast tissue 3 can be assessed visually by the advantageously visually transparent plate of the paddle. The haptic and/or sensitivity evaluation takes places by consultation with the patient.

Step c of the illustrated example embodiment comprises adjusting the first compression to the target compression, wherein adjusting comprises exerting a manual force $F_m$ on the paddle 21. In particular, adjusting can comprise increasing or reducing the first compression of the breast tissue 3. In particular, adjusting can comprise adjusting the distance between the paddle 21 and the stage 24. In particular, exerting the manual force $F_m$ on the paddle 21 can comprise pressing on the paddle 21 or pulling on the paddle 21.

Figure 5:
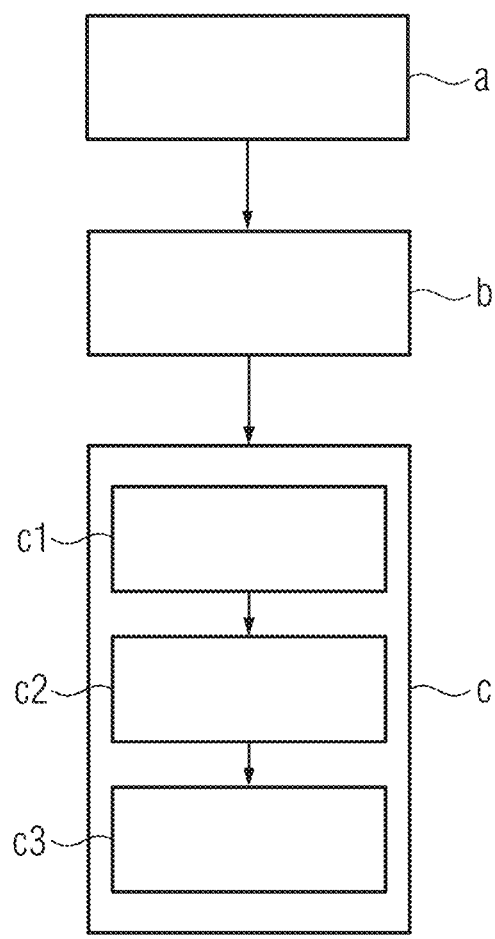
FIG. 5: shows a second flowchart of a further example embodiment of the inventive method for compression of breast tissue.

FIG. 5 shows a second flowchart of a further example embodiment of the inventive method for compression of breast tissue 3.

Steps a and b are carried out analogously to the description in FIG. 4. In this example embodiment, the step c is divided into three substeps c1, c2, c3. Sub-steps c1, c2 c3 are carried out analogously to the description of steps in FIGS. 2 and 3.

Figure 6:
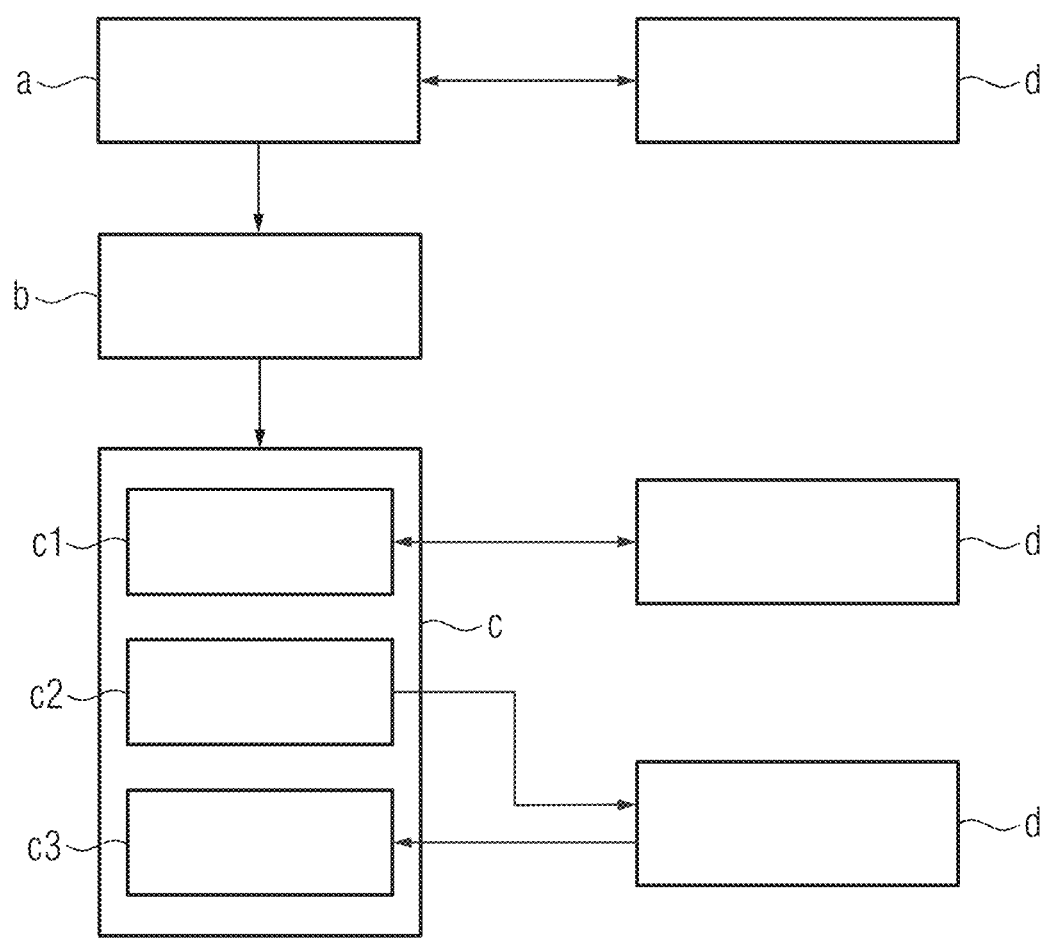
FIG. 6: shows a third flowchart of a further example embodiment of the inventive method for compression of breast tissue.

FIG. 6 shows a third flowchart of a further example embodiment of the inventive method for compression of breast tissue 3.

Steps a, b, c comprising substeps c1, c2, c3 are carried out according to the descriptions relating to FIGS. 2, 3 and 4.

In this example embodiment, step d is carried out between individual steps a, b, c comprising substeps c1, c2, c3. Step d comprises detecting a force sum $F_{Sum}$ of a value of a paddle compression force $F_{Pad}$ and a manual force $F_m$, acting on the paddle 21 from a force via a first force sensor, which is arranged on a paddle 21. This step can be carried out at different positions of the method. In particular, step d can be carried out several times during the method. Step d is used to check the force sum $F_{Sum}$ acting on the paddle 21.

Step d is carried out continuously or in discrete intervals as step a is being carried out. When step d is carried out in discrete intervals, step d can be carried out, for example, every 500 ms as step a is carried out. To ensure that when generating the first compression in step a, a reference compression force $ref_0$ acts on the breast tissue through the paddle, the force sum $F_{Sum}$ on the paddle is measured via the first force sensor. If the paddle 21 exerts the reference compression force $ref_0$ or the paddle compression force $F_{Pad}$ on the breast tissue 3, the breast tissue 3 also exerts a force with the value of the reference compression force $ref_0$ or the value of the paddle compression force $F_{Pad}$ on the paddle 21. Since the manual force $F_m$ is zero in step a, the force sum $F_{Sum}$ is equal to the value of the paddle compression force $F_{Pad}$. The paddle compression force $F_{Pad}$ should match, in particular, the reference compression force $ref_0$. For generating the first compression, the force detected by the first force sensor, in other words, the force sum $F_{Sum}$, has to match the value of the reference compression force ref, therefore.

Analogously, step d is carried out continuously or in discrete intervals as step c1 is being carried out. Due to exertion of the manual force $F_m$ on the paddle 21 the force sum $F_{Sum}$ detected by the first force sensor no longer matches the value of the reference compression force $ref_0$. As described above, a paddle position is adjusted in step c1 in such a way that in step d, the force sum $F_{Sum}$ matches the value of the reference compression force $ref_0$.

After removing the manual force $F_m$ in step c2, the value of the reference compression force is replaced in step c3 by the force sum $F_{Sum}$. The force sum $F_{Sum}$ on the paddle is also detected for this purpose in step d and this value is set as a new value for the reference compression force $ref_1$.

Figure 7:
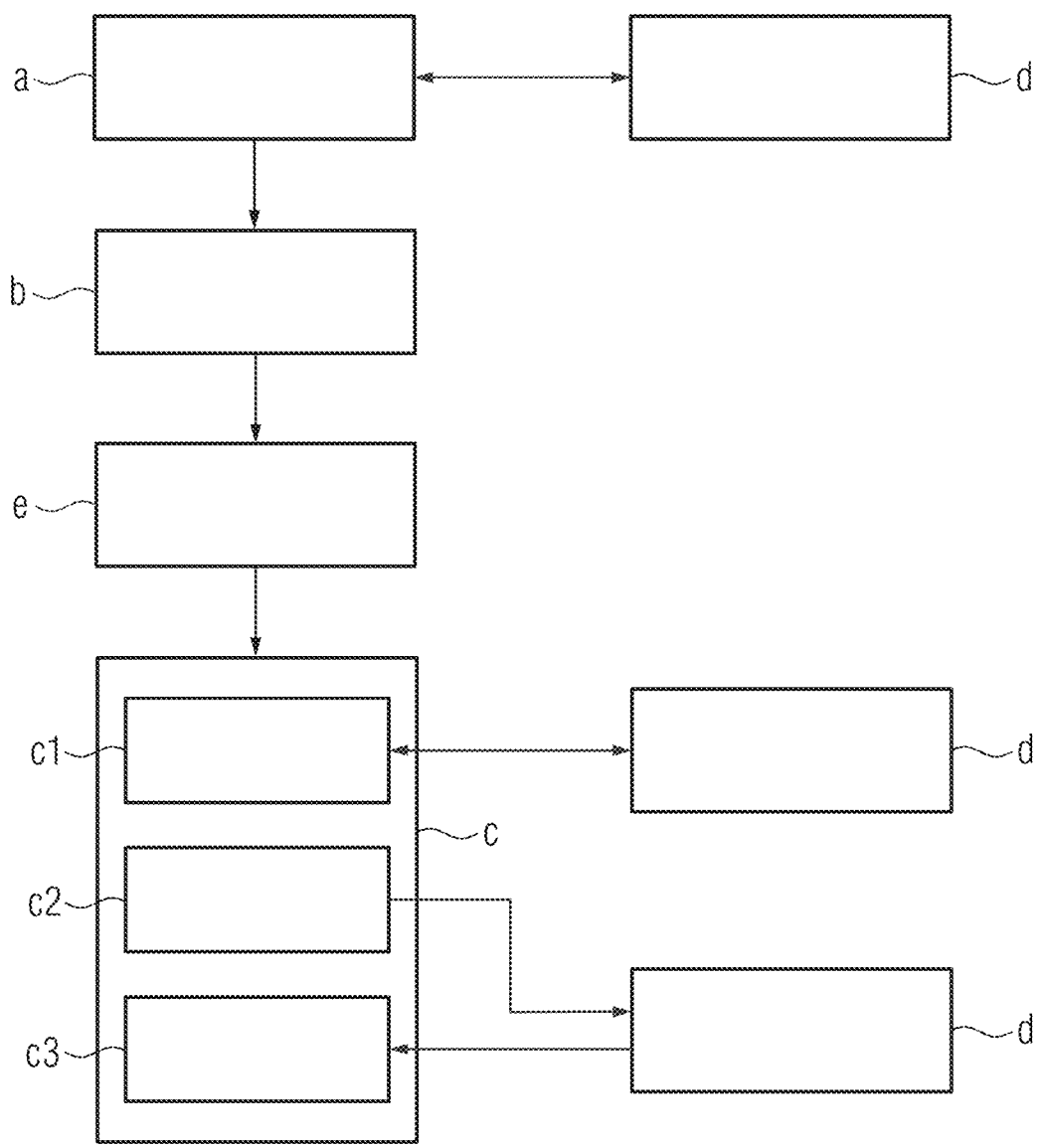
FIG. 7: shows a fourth flowchart of a further example embodiment of the inventive method for compression of breast tissue.

FIG. 7 shows a fourth flowchart of a further example embodiment of the inventive method for compression of breast tissue 3.

Steps a, b, c, comprising substeps c1, c2, c3 are carried out according to the descriptions relating to the FIGS. 2, 3 and 4. Step d is carried out according to the description relating to FIG. 7. Before carrying out step c comprising the substeps c1, c2, c3, step e, which comprises detecting whether a manual force $F_m$ is acting on a paddle 21 [ ]. In particular, it is thus possible to differentiate between an intentional force on the paddle 21, an unintentional force on the paddle 21 and a force on the paddle 21 due to an article. In particular, the intentional force corresponds to a manual force $F_m$. In particular, the unintentional force can be exerted by accidentally touching or leaning on the paddle 21. Alternatively, a force can be exerted on the paddle 21 due to an article, which presses onto the paddle 21, falls onto the paddle 21, etc. In particular, with an unintentional force on the paddle or a force on the paddle due to an article there should be no adjusting of the first compression.

In particular, detecting in step e can take place in three variants, which are combined with each other.

In a first variant, detecting can take place via a capacitive sensor arranged on the paddle 21. The capacitive sensor can comprise at least one capacitor. In particular, the capacitive sensor can register or detect a drop in the electrical capacitance of the capacitor. In particular, a drop in the electrical capacitance can be caused by the capacitive sensor being touched by a conductive article. In particular, an article of this kind can be a human hand. In particular, articles, which can drop onto the paddle 21 or can press onto the paddle 21, are typically non-conductive. In particular, step c or its substeps c1, c2, c3 are only carried out if the capacitive sensor detects a drop in the electrical capacitance. In particular, an operator has to touch the paddle 21 at the capacitive sensor in order to carry out adjusting of the first compression. In particular, this leads to a drop in the electrical capacitance at the sensor. With an unintentional force or a force due to an article the capacitive sensor typically does not detect a drop in the electrical capacitance. Consequently, no adjustment of the first compression is carried out.

In a second variant, the paddle 21 comprises a second force sensor, which detects or registers only the manual force Fm on the paddle. The operator has to exert the manual force Fm on the paddle 21 in such a way that the second force sensor detects the force. This is advantageously possible in only a small area of the paddle. Step c and its substeps c1, c2, c3 is only carried out if the second force sensor detects the manual force Fm. An unintentional force or a force due to an article is, in particular, not exerted in such a way that the second force sensor can register or detect it. Consequently, no adjustment of the first compression is carried out in the case of an unintentional force or a force due to an article.

In a third variant, the paddle 21 comprises a switch. In particular, the operator has to activate the switch during exertion of the manual force Fm. Step c and its substeps c1, c2, c3 is only carried out if the switch is activated. An unintentional force or a force due to an article typically does not activate the switch, so no unintentional adjustment of first compression is carried out.

Figure 8:
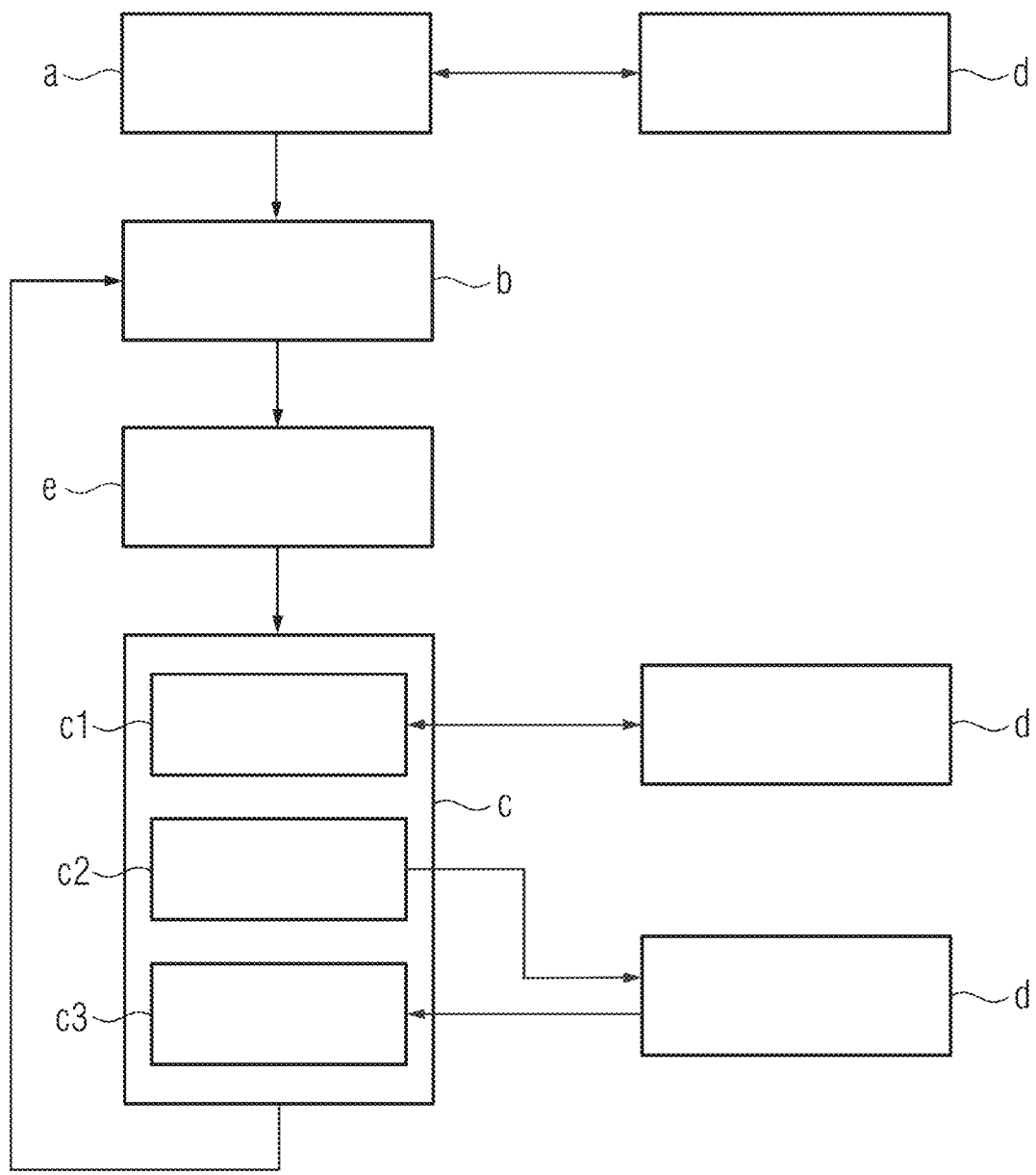
FIG. 8: shows a fifth flowchart of a further example embodiment of the inventive method for compression of breast tissue.

FIG. 8 shows a fifth flowchart of a further example embodiment of the inventive method for compression of breast tissue 3.

In particular, the method in the illustrated example embodiment is carried out according to the example embodiment in FIG. 7. In particular, the method in the illustrated example embodiment comprises a control loop. In particular, after carrying out step c comprising the substeps c1, c2, c3, step b is carried out again. In step b, a first compression adjusted in a first loop pass is compared again with a target compression. This control loop is performed until this comparison results in a match between the first compression and the target compression.

Figure 9:
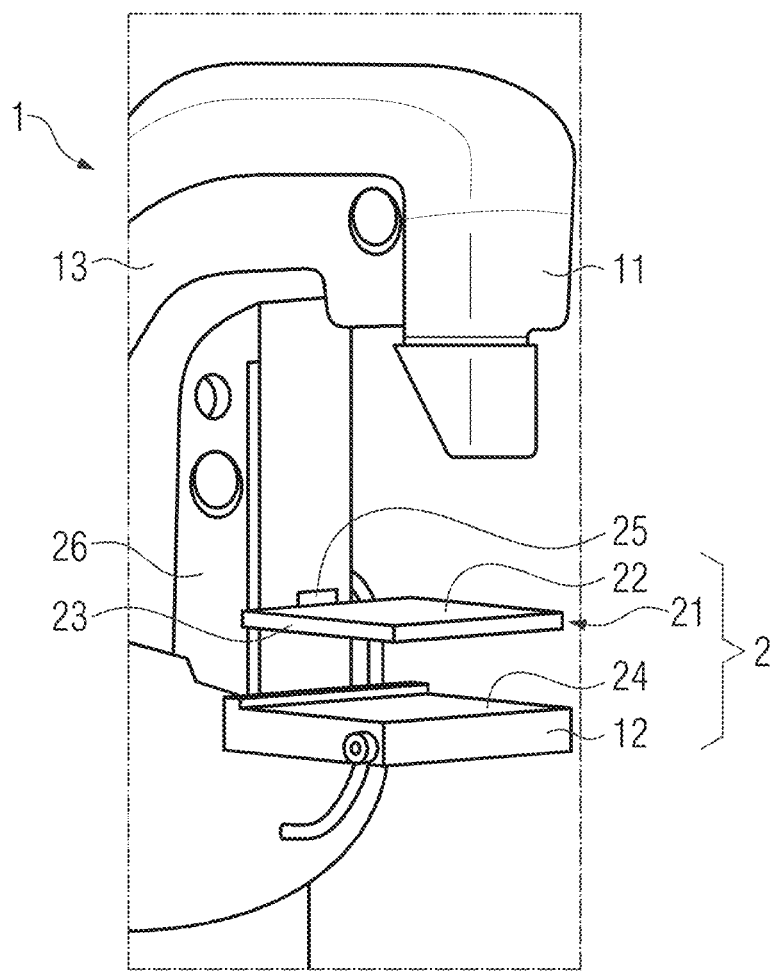
FIG. 9: shows an example embodiment of an inventive mammography system comprising an inventive compression system for compression of breast tissue.

FIG. 9 shows an example embodiment of an inventive mammography system 1 comprising an inventive compression system for compression of breast tissue 3.

The mammography system 1 comprises an X-ray source 11, an X-ray detector 12 and a compression system 2, which are arranged on a stand 13. In particular, the X-ray source 11 is arranged vertically spaced apart from the X-ray detector 12. In other words, the X-ray source 11 is arranged above the X-ray detector 12. In particular, the compression system 2 is arranged between the X-ray source 11 and the X-ray detector 12. In particular, the compression system 2 comprises a paddle 21, a stage 24, a first force sensor 25 and a control unit 26. In particular, the stage 24 is arranged on the side of the X-ray detector 12 facing the rays. Alternatively, the side of the X-ray detector 12 facing the rays can be designed as a stage 24. In particular, the paddle 21 comprises a plate 22 and a frame 23. The plate 22 of the paddle 21 is connected via the frame 23 to the stand 13. In particular, the paddle 21 can be adjusted or positioned vertically along the stand 13. Adjusting is controlled by a control unit 26. In particular, the frame 23 can be connected at three sides to the plate 22 of the paddle 21. Advantageously, the frame 23 is not connected to the plate 22 on the side at which the patient stands at the paddle 21. In particular, the plate 22 is clamped in the frame 23. In particular, a first force sensor 25, which detects all forces acting vertically on the paddle 21, is arranged on the paddle 21.

Although the invention has been illustrated and described in detail with reference to the preferred example embodiments it is not limited hereby. A person skilled in the art can derive other variations and combinations herefrom without deviating from the fundamental idea of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for compression of breast tissue arranged between a paddle and a stage of a compression system for a mammography examination, comprising:
generating a first compression of the breast tissue by building up a reference compression force by adjusting the paddle relative to the stage;
comparing the first compression with a target compression; and
adjusting the first compression to the target compression, the adjusting including exerting a manual force on the paddle.

2. The method of claim 1, further comprising:
detecting a force sum acting on the paddle of a force with a value of a paddle compression force and the manual force, via a first force sensor arranged on the paddle.

3. The method of claim 2, wherein the adjusting, including the exerting of the manual force on the paddle, comprises:
adjusting a paddle position as a function of the force sum detected by the first force sensor, so that the force sum matches a value of the reference compression force.

4. The method of claim 3, wherein the adjusting, including the exerting of the manual force on the paddle, further comprises:
removing the manual force, and
adjusting the value of the reference compression force to the force sum.

5. The method of claim 2, wherein the adjusting is only carried out if a difference between a value of the reference compression force and the force sum exceeds a threshold value.

6. The method of claim 1, further comprising:
detecting whether a manual force is acting on the paddle.

7. The method of claim 6, wherein the detecting of whether the manual force is acting on the paddle, takes place via a capacitive sensor arranged on the paddle.

8. The method of claim 6, wherein the detecting of whether the manual force is acting on the paddle, takes place via a second force sensor arranged on the paddle.

9. The method of claim 6, wherein the detecting of whether the manual force is acting on the paddle, takes place via a switch arranged on the paddle.

10. The method of claim 4, wherein
the adjusting of the value of the reference compression force is only carried out upon the force sum being less than or equal to a maximum compression force value, and
adjusting, upon the force sum being greater than the maximum compression force value, the value of the reference compression force to the maximum compression force value.

11. The method of claim 1, wherein the target compression in fulfils at least one of:
crease-free compression of the breast tissue,
uniform compression of the breast tissue,
pain-free compression of the breast tissue.

12. The method of claim 1, wherein the method is carried out in a control loop.

13. A compression system for a mammography system, comprising a stage;
a paddle, designed to compress breast tissue arranged between the paddle and the stage;
a first force sensor arranged on the paddle, designed to measure a force sum on the paddle; and
at least one processor, designed to generate control signals for generating at least one of a first compression and a target compression of the breast tissue for a mammography examination, wherein the at least one processor is configured to
generate the first compression of the breast tissue by building up a reference compression force by adjusting the paddle relative to the stage and compare the first compression with a target compression, subsequent adjusting of the first compression to the target compression including exerting a manual force on the paddle.

14. The compression system of claim 13, wherein the paddle comprises a capacitive sensor, designed to detect a touch.

15. The compression system of claim 14, wherein the paddle comprises a second force sensor, designed to detect the manual force on the paddle.

16. The compression system of claim 13, wherein the paddle comprises a switch, designed to measure the manual force on the paddle.

17. A mammography system comprising
the compression system of claim 13;
an X-ray source;
an X-ray detector.

18. The method of claim 2, further comprising:
detecting whether a manual force is acting on the paddle.

19. The method of claim 18, wherein the detecting of whether the manual force is acting on the paddle, takes place via a capacitive sensor arranged on the paddle.

20. The method of claim 18, wherein the detecting of whether the manual force is acting on the paddle, takes place via a second force sensor arranged on the paddle.

21. The method of claim 18, wherein the detecting of whether the manual force is acting on the paddle, takes place via a switch arranged on the paddle.

22. The method of claim 2, wherein the target compression in fulfils at least one of:
crease-free compression of the breast tissue,
uniform compression of the breast tissue,
pain-free compression of the breast tissue.

23. The compression system of claim 13, wherein the paddle comprises a force sensor, designed to detect the manual force on the paddle.

24. The compression system of claim 14, wherein the paddle comprises a switch, designed to measure the manual force on the paddle.

25. The compression system of claim 15, wherein the paddle comprises a switch, designed to measure the manual force on the paddle.

* * * * *